United States Patent
Hoyne et al.

[11] Patent Number: 6,042,558
[45] Date of Patent: Mar. 28, 2000

[54] SAPHENOUS VEIN HARVESTING SUPPORT

[75] Inventors: William Hoyne, Oak Forest, Ill.;
Steven R. Lamb, Union City, Calif.

[73] Assignee: Orthopedic Systems, Inc., Union City, Calif.

[21] Appl. No.: 09/173,479

[22] Filed: Oct. 14, 1998

[51] Int. Cl.$^7$ .................................................. A61F 13/00
[52] U.S. Cl. ................... 602/61; 602/60; 602/62
[58] Field of Search ............. 606/159; 600/104; 602/60, 62, 61

[56] References Cited

U.S. PATENT DOCUMENTS

| | | | |
|---|---|---|---|
| 4,669,450 | 6/1987 | Lindberg | 601/35 |
| 5,258,019 | 11/1993 | Riddle et al. | 606/142 |
| 5,695,514 | 12/1997 | Chin | 606/190 |
| 5,814,059 | 9/1998 | Hart et al. | 606/190 |
| 5,817,013 | 10/1998 | Ginn et al. | 600/114 |
| 5,848,992 | 12/1998 | Hart et al. | 604/167 |
| 5,899,912 | 5/1999 | Eaves, III et al. | 606/159 |
| 5,928,135 | 7/1999 | Knight et al. | 600/104 |
| 5,928,138 | 7/1999 | Knight et al. | 600/201 |

*Primary Examiner*—Gary Jackson
*Attorney, Agent, or Firm*—Theodore J. Bielen, Jr.

[57] ABSTRACT

A patient support for harvesting a saphenous vein utilizing a base member that has an outwardly extending upper element. The upper element includes at least one surface with an edge portion. The edge portion is intended for contacting a portion of the leg and applying pressure to the soft tissue of the leg to provide surgical access to the saphenous vein by shifting the soft tissue relative to a leg bone.

15 Claims, 3 Drawing Sheets

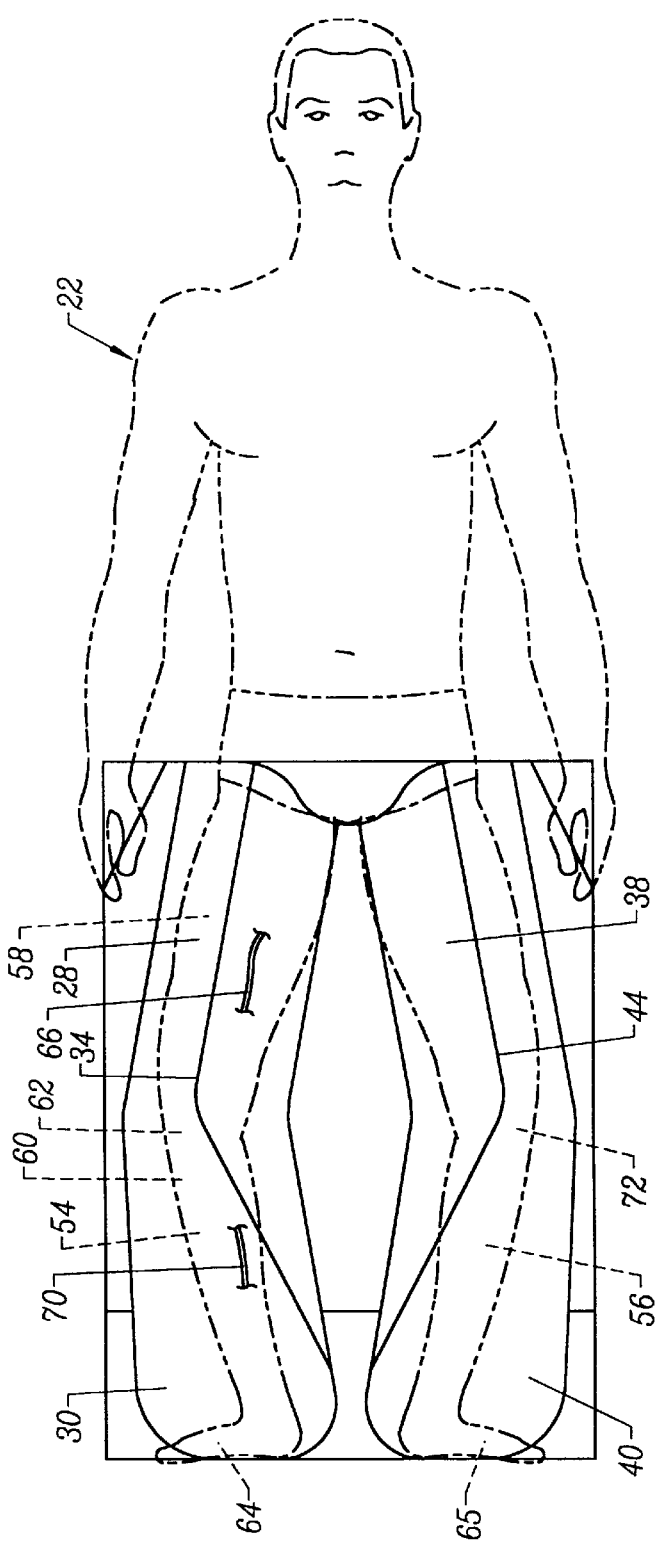
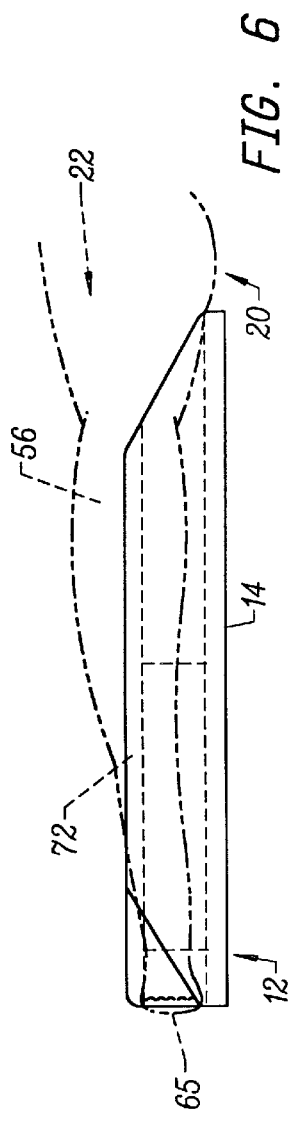

SAPHENOUS VEIN HARVESTING SUPPORT

BACKGROUND OF THE INVENTION

The present invention relates to a patient support device to permit harvesting of a saphenous vein.

Cardiac surgery often requires grafting of veins for use as a bypass. In the past, surgeons have harvested portions of the saphenous vein found in the leg of the patient. Generally, the saphenous vein may be taken from either leg of the patient or both legs of the patient, dependent on the amount of vein material needed for the cardiac surgery.

The prior harvesting methods have encountered difficulty in removing the saphenous vein since the soft tissue of the femoral portion of the leg adjacent the saphenous vein tends to lie underneath the patient when the patient is in a supine position. Rotation of the soft tissue of the leg by an the surgeon or an assistant has been necessary in order to reach the saphenous vein for harvesting in the past, which is an awkward procedure. This procedure has entailed the use of rolled towels, which tends to dislodge during the harvesting procedure.

A support for a patient which permits the easy harvesting of the saphenous vein would be a notable advance in the medical field.

SUMMARY OF THE INVENTION

In accordance with the present invention a novel and useful support for a patient for harvesting a saphenous vein is herein provided.

The support of the present invention utilizes a base member which is capable of lying on a surface such as a surgery table. Connected or formed unitarily with respect to the base member is an outwardly extending upper element. The upper element would also extend upwardly, if the patient is lying prone on a surgery table. The upper element includes a first surface with an edge portion for contacting the leg of the patient. A second surface may also formed adjacent the first surface with a vertical separation between the first and second surfaces by the edge portion. The first surface is positioned further outwardly from the base member than the second surface. Thus, the second surface may be perceived as lying in a trough relative to the first surface that is lying on a plateau. The edge portion between the first and second surfaces contacts the leg of the patient, generally between the hip and ankle i.e. along the entire length of the leg. Such pressure causes the leg to splay into the trough containing the second surface. Such splaying shifts, rotates, or pushes the soft tissue of the tibial and femoral portions of the leg upwardly, relative to a leg bone, for surgical access to the saphenous vein.

The support of the present invention may also include third and fourth surfaces which are positioned symmetrically on the base member to provide access to the saphenous vein of the other leg of the patient. Thus, the surgeon is able to choose either leg, or both legs, for the harvesting of saphenous veins during cardiac surgery.

The end of the base member may be angled to provide a sloping surface, which generally supports the buttocks region of the patient when the patient is lying on the support of the present invention. In addition, a projection may lie between the first and third surfaces to further position the patient on the support. It should also be noted that the edge portion between either the first and second surfaces, or the third and fourth surfaces, is angled, in plan view. This assures contact of the leg of the user between the knee and ankle, resulting in the splaying of the foot within the trough formed by the second and fourth surfaces. In this manner, the support of the present invention forces the knees of the user to flex upwardly and outwardly with external rotation of the foot, into the troughs or chambers formed by the second and fourth surfaces, with the heels adjacent one another. Thus, the leg soft tissue of the patient is perfectly positioned for harvesting of a saphenous vein or veins.

It may be apparent that a novel and useful patient support for harvesting a saphenous vein has been described.

It is therefore an object of the present invention to provide a support for a patient which permits the presentation or access to the soft tissue region of the leg for harvesting of a saphenous vein during cardiac surgery.

Another object of the present invention is to provide a patient support for harvesting a saphenous vein which may be easily adaptable to a conventional surgery table used for cardiac surgery.

A further object of the present invention is to provide a support for a patient undergoing cardiac surgery in order to harvest saphenous vein material, which eliminates the need for the surgeon, or surgical assistant, to rotate the legs of the user to gain access to the soft tissue harboring the saphenous vein.

Yet another object of the present invention is to provide a patient support for harvesting a saphenous vein during cardiac surgery which rotates the legs of the user to an accessible position without employing movable parts.

The invention possesses other objects and advantages especially as concerns particular characteristics and features thereof which will become apparent as the specification continues.

BRIEF DESCRIPTION OF THE DRAWINGS

FIG. 5 is a top plan view of the support of the present invention with a patient positioned thereupon.

FIG. 6 is a side elevational view of the support of the present invention showing the patient positioned, in part, thereupon.

For a better understanding of the invention references made to the following detailed description of the preferred embodiments thereof which should be taken in conjunction with the prior described drawings.

DETAILED DESCRIPTION OF THE PREFERRED EMBODIMENTS

Various aspects of the present invention will evolve from the following detailed description of the preferred embodiments, which should be taken in conjunction with the hereinbefore described drawings.

Figure 1:
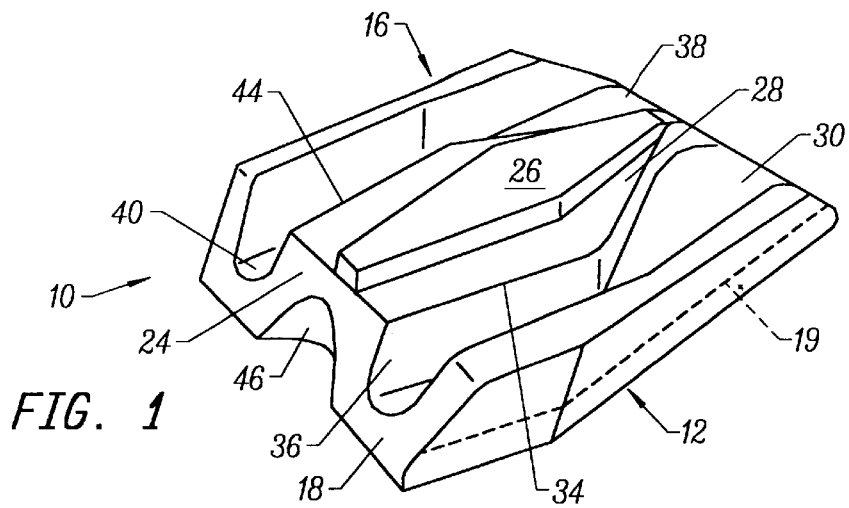
FIG. 1 is a top right perspective view of the support of the present invention.
Figure 2:
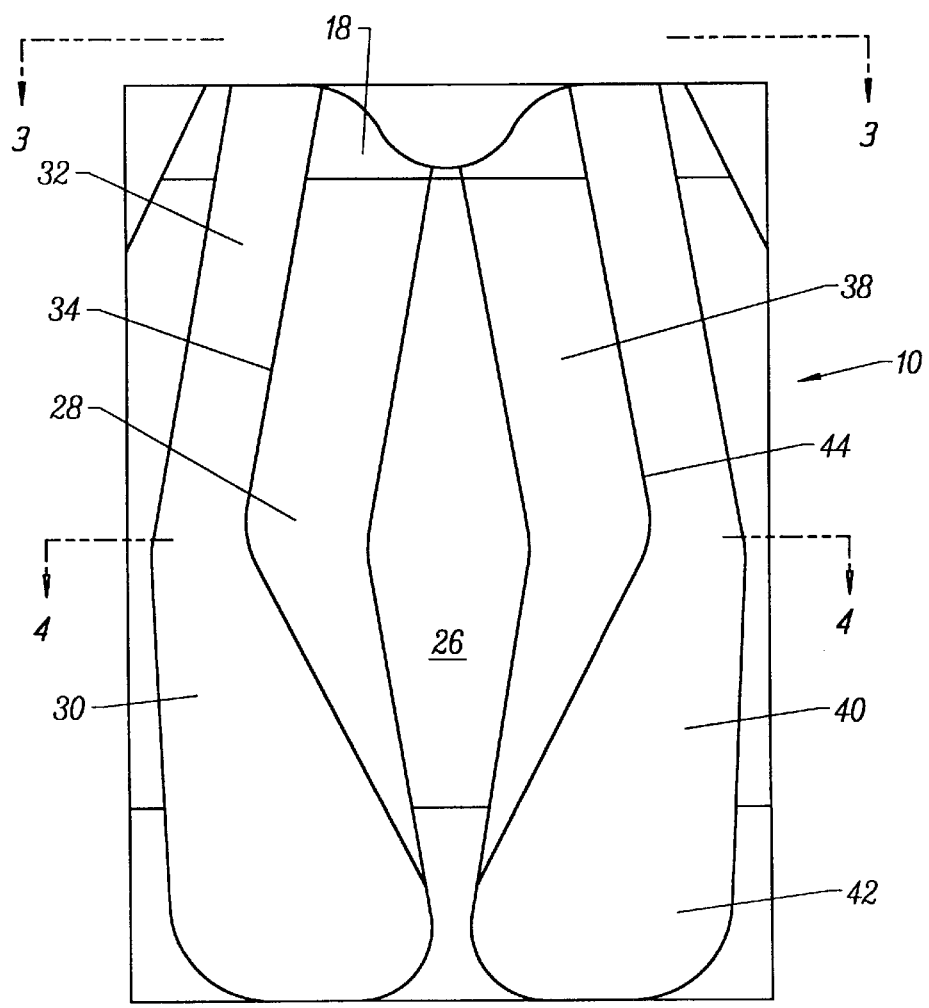
FIG. 2 is a top plan view of the support of the present invention.

With reference to FIG. 1, it may be observed that the support 10 of the present invention is shown. Support 10 is formed with a base 12 having a base surface 14. Connected to base member 12 is an upper element 16. Dashed line 19 generally marks the transition between upper element 16 and base 12, although base member 12 and upper element 16 may be formed contiguously, as is the case in the embodiment shown in FIGS. 1–6. Support 10 may be formed of a single material such as a relatively firm foam, or may include a mixture of materials, some being relatively stiff and others being relatively flexible. Base member 12 is formed with a slopped or mitred end 18 which generally contacts the buttocks and upper thigh regions 20 of the patient 22, best shown in FIG. 6.

Upper element 16 extends outwardly from base member 12. A plateau 24 extends outwardly from base surface 14. A roughly diamond shaped projection 26 partitions plateau 24. A first surface 28 forms on one side of projection 26. A second surface 30 lies in a chamber or trough 32 adjacent first surface 28. Edge portion 34 separates first and second surfaces 28 and 30 from one another, FIG. 2. Thus, a wall 36, FIG. 1, is formed between first surface 28 and second surface 30. It should be noted that edge portion 34 is angled, the importance of which will be discussed hereinafter. Likewise, third surface 38 lies on the opposite side of diamond shaped projection 26 and is separated from a fourth surface 40 in a trough 42 by edge portion 44, which is also angled. With respect to FIG. 2, it may be observed that edge portions 34 and 44 are the mirror image of one another when viewed on FIG. 2. Cavity 46 is constructed at sloped end 18 of base member 12 for the ease of positioning support 10 by the user. Wall 48 separates third surface 38 from fourth surface 4, FIG. 3.

Figure 3:
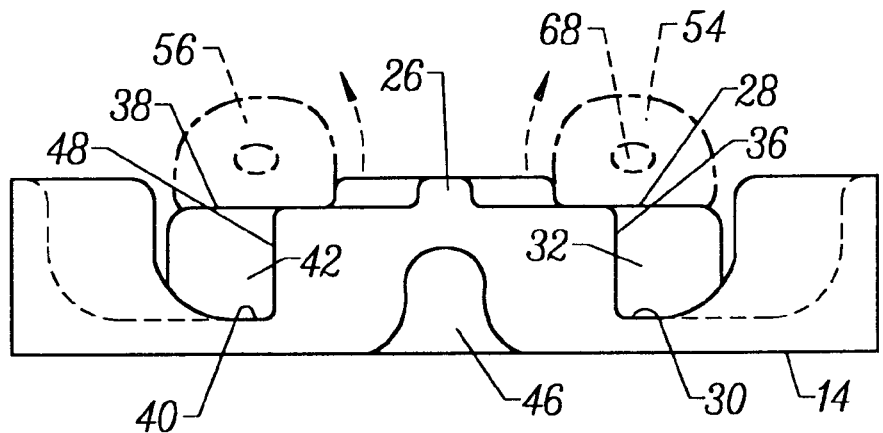
FIG. 3 is an end view taken along line 3—3 of FIG. 2.
Figure 4:
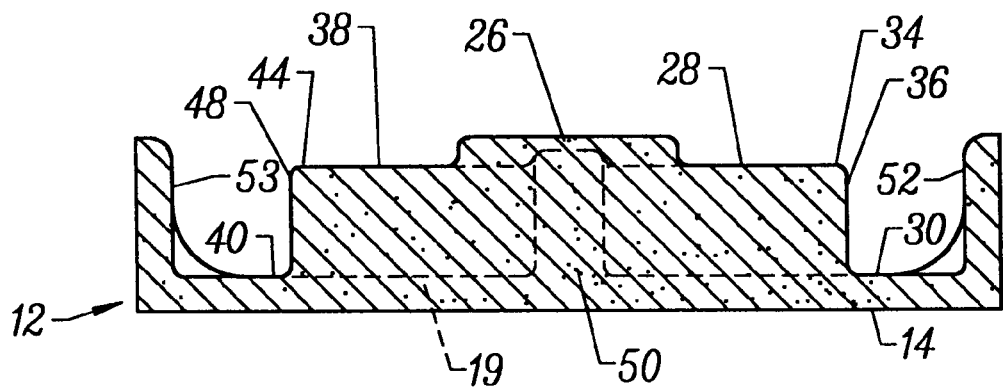
FIG. 4 is a sectional view taken along line 4—4 of FIG. 2.

Referring to FIGS. 3 and 4, it may be seen that troughs 32 and 42 follow, generally, the contours determined by edge portions 34 and 44. In addition, base member 12 may include an internal central boss 50, which is of stiffer configuration than the upper element 16, FIG. 4. Walls 52 and 53 may also be fairly rigid in order to support the patient 22. FIG. 3 depicts legs 54 and 56, of patient 22, in phantom.

In operation, the surgeon or surgical assistant, places support 10 on an operating table, usually prior to cardiac surgery. The patient is then positioned on support 10 according to FIGS. 3, 5, and 6. That is to say, buttocks 20 of patient 22 generally lies on sloped surface 18. The femoral portion of leg 54 lies mostly on first surface 28. Edge portion 34 underlies femoral portion 58 of leg 54. Tibial portion 60 of leg 54 also contacts edge portion 34. However, most of the tibial portion 60 of leg 54 rests on second surface 30, in a trough, since edge portion 34 underlies tibial portion 60 near the knee 62 of leg 54. Said positioning of tibial portion 60 of leg 54 causes the foot 64 to splay or flip over on its side. The same splaying takes place with respect to foot 65 of leg 56. The knees 62 and 72 are also separated at this time. The splaying of foot 64 is also accompanied by the shifting or rotation on the soft tissue relative to leg bone 68 (FIG. 3) found of leg 54. Thus, the saphenous veins 66 and 70, shown in portion on FIG. 5, are readily available to the surgeon for harvesting. In other words, the splaying of foot 64 and the flexion and rotation of knee 62 results in a pressure being applied to the posterior thigh of leg 54 to push the soft tissue of leg 54 upwardly, resulting in the medial aspect of the thigh and calf of patient 22 to lie somewhat parallel to first surface 28. That is to say, the soft tissue of legs 54 shifts relative to bone 68. In any case, support 10 produces the optimal surgical access to saphenous veins 66 and 70, allowing the surgeon to work on an essentially flat surface such as surface 28 instead of the naturally inclined surface of the medial thigh, an awkward situation which was the case in the prior art. The same positioning takes place with respect to leg 56, relative to third and fourth surfaces, 38 and 56, respectively.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A patient support for harvesting a saphenous vein, the support, comprising:
   a. a base member; and
   b. an outwardly extending upper element connected to said base member, said upper element including a surface shaped to contact the leg of a patient, said surface further including an edge portion contacting one leg of the patient forcing the soft tissue adjacent the saphenous vein to shift relative to a bone of the leg of the patient in the vicinity of the saphenous vein, said shifted soft tissue being accessible for harvesting a saphenous vein, said base member and connected upper element further comprising an end surface angled between said base member and said upper element.

2. The support of claim 1 in which said surface is a first surface, and said outwardly extending upper element further comprises a second surface adjacent said first surface, said edge portion lying between said first and second surfaces.

3. The support of claim 2 in which said second surface of said upper element includes a chamber allowing the foot of the patient to splay.

4. The support of claim 3 which additionally comprises stop means for limiting said splay of the foot of the patient.

5. The support of claim 4 in which said means for limiting said splay of the foot of the patient comprises a protuberance on extending outwardly relative to said base member.

6. The support of claim 2 in which said outwardly extending upper element of said base member in constructed of flexible material.

7. The support of claim 1 which additionally comprises a projection connected to said upper element and extending outwardly therefrom adjacent to said first surface.

8. The support of claim 7 which additionally comprises a projection connected to said upper element and extending outwardly therefrom, between said first and third surfaces.

9. The support of claim 1 in which said outwardly extending upper element of said base member is constructed of flexible material.

10. A patient support for harvesting a saphenous vein, the support, comprising:
    a. a base member; and
    b. an outwardly extending upper element connected to said base member, said upper element including a first surface shaped to contact the leg of a patient, said surface further including an edge portion contacting one leg of the patient forcing the soft tissue adjacent the saphenous vein to shift relative to a bone of the leg of the patient in the vicinity of the saphenous vein, said shifted soft tissue being accessible for harvesting a saphenous vein; and
    c. said upper element further including a second surface adjacent said first surface, said edge portion lying between said first and second surfaces, said second surface of said upper element including a chamber allowing the foot of the patient to splay.

11. The support of claim 10 in which said base member and connected upper element further comprise an end surface angled between said base member and said upper element.

12. The support of claim 11 which additionally comprises a projection connected to said upper element and extending outwardly therefrom adjacent to said first surface.

13. The support of claim 12 which further includes a third surface, a fourth surface, and an edge portion therebetween, said third surface positioned further outwardly from said base member than said fourth surface, said edge portion between said third and fourth surfaces intended to contact another leg of the patient with the application of pressure on the soft tissue adjacent the saphenous vein.

14. The support of claim 13 in which said edge portion between said third and fourth surfaces forms an angle, one leg of said angle contacting the leg of the patient between the hip and ankle.

15. A patient support for harvesting a saphenous vein, the support, comprising:
   a. a base member; and
   b. an outwardly extending upper element connected to said base member, said upper element including a first surface shaped to contact the leg of a patient, said surface further including an edge portion contacting one leg of the patient forcing the soft tissue adjacent the saphenous vein to shift relative to a bone of the leg of the patient in the vicinity of the saphenous vein, said shifted soft tissue being accessible for harvesting a saphenous vein; and
   c. said upper element further including a second surface adjacent said first surface, said edge portion lying between said first and second surfaces, said edge portion between said first and second surface forming an angle, one leg of said angle contacting the leg of the patient between the hip and ankle.

* * * * *